US00PP35490P2

(12) United States Plant Patent
de Vos

(10) Patent No.: US PP35,490 P2
(45) Date of Patent: Nov. 21, 2023

(54) ***HYDRANGEA* PLANT NAMED 'HSE1735301'**

(50) Latin Name: *Hydrangea serrata*
Varietal Denomination: HSE1735301

(71) Applicant: KWEKERIJ LENDERT de VOS B.V., Reeuwijk (NL)

(72) Inventor: Lendert de Vos, Reeuwijk (NL)

(73) Assignee: KWEKERIJ LENDERT de VOS B.V., Reeuwijk (NL)

( * ) Notice: Subject to any disclaimer, the term of this patent is extended or adjusted under 35 U.S.C. 154(b) by 0 days.

(21) Appl. No.: 18/102,970

(22) Filed: Jan. 30, 2023

Related U.S. Application Data

(60) Provisional application No. 63/321,093, filed on Mar. 17, 2022.

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — C. Anne Whealy

(57) ABSTRACT

A new and distinct cultivar of *Hydrangea* plant named 'HSE1735301', characterized by its upright to broadly spreading plant habit; freely branching habit; strong and sturdy stems; dark green-colored leaves; freely flowering habit; lace-cap inflorescences with white to greenish white-colored sterile flowers and light violet-colored fertile flowers; and good garden performance.

2 Drawing Sheets

Figure 1:
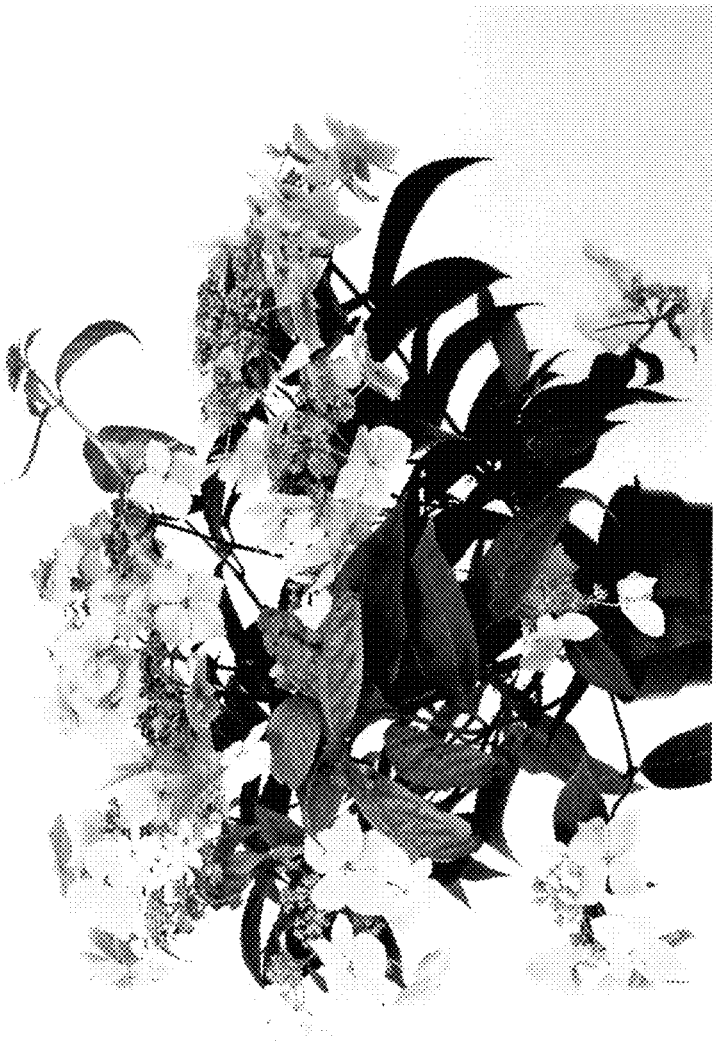

Botanical designation: *Hydrangea serrata.*
Cultivar denomination: 'HSE1735301'.

CROSS-REFERENCED TO CLOSELY-RELATED APPLICATIONS

An European Community Plant Breeder's Rights application for this plant was filed by the Applicant/Assignee of the instant application, Kwekerij Lendert de Vos of Reeuwijk, The Netherlands on Jan. 25, 2022, application number 2022/0236. Foreign priority is not claimed to this European Plant Breeder's Rights application.

BACKGROUND OF THE INVENTION

The present invention relates to a new and distinct cultivar of *Hydrangea* plant, botanically known as *Hydrangea serrata*, commercially referred to as a Mountain *Hydrangea*, and hereinafter referred to by the name 'HSE1735301'.

The new *Hydrangea* plant is a product of a planned breeding program conducted by the Inventor in Reeuwijk, The Netherlands. The objective of the breeding program is to create new compact and strong *Hydrangea* plants with attractive inflorescences and good postproduction longevity.

The new *Hydrangea* plant originated from a cross-pollination conducted by the Inventor during the summer of 2016 of a proprietary selection of *Hydrangea serrata* identified as code number 12-00-203, not patented, as the female, or seed, parent with a proprietary selection of *Hydrangea serrata* identified as code number 12-00-205, not patented, as the male, or pollen, parent. The new *Hydrangea* plant was discovered and selected as a single flowering plant from within the progeny of the stated cross-pollination in a controlled greenhouse environment in Reeuwijk, The Netherlands in August, 2017.

Asexual reproduction of the new *Hydrangea* plant by terminal vegetative cuttings since August, 2018 in a controlled greenhouse environment in Reeuwijk, The Netherlands has shown that the unique features of this new *Hydrangea* plant are stable and reproduced true to type in successive generations of asexual reproduction.

SUMMARY OF THE NEW PLANT

Plants of the new *Hydrangea* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'HSE173530'. These characteristics in combination distinguish 'HSE1735301' as a new and distinct *Hydrangea* plant:

1. Upright to broadly spreading plant habit.
2. Freely branching habit.
3. Strong and sturdy stems.
4. Dark green-colored leaves.
5. Freely flowering habit.
6. Lace-cap inflorescences with white to greenish white-colored sterile flowers and light violet-colored fertile flowers.
7. Good garden performance.

Plants of the new *Hydrangea* can be compared to plants of the female parent selection. Plants of the new *Hydrangea* differ primarily from plants of the female parent selection in the following characteristics:

1. Leaves of plants of the new *Hydrangea* are darker green in color than leaves of plants of the female parent selection.

2. Sterile flowers of plants of the new *Hydrangea* are white to greenish white in color whereas sterile flowers of plants of the female parent selection are light pink in color.
3. Apices of sterile flowers of plants of the new *Hydrangea* are more acute than and not as rounded as apices of sterile flowers of plants of the female parent selection.

Plants of the new *Hydrangea* can be compared to plants of the male parent selection. Plants of the new *Hydrangea* differ primarily from plants of the male parent selection in the following characteristics:

1. Leaves of plants of the new *Hydrangea* are darker green in color than leaves of plants of the male parent selection.
2. Sterile flowers of plants of the new *Hydrangea* are white to greenish white in color whereas sterile flowers of plants of the male parent selection are light pink in color.
3. Apices of sterile flowers of plants of the new *Hydrangea* are more acute than and not as rounded as apices of sterile flowers of plants of the male parent selection.

Plants of the new *Hydrangea* can be compared to plants of *Hydrangea serrata* 'Bluebird', not patented. In side-by-side comparisons, plants of the new *Hydrangea* differ primarily from plants of 'Bluebird' in the following characteristics:

1. Leaves of plants of the new *Hydrangea* are darker green in color than leaves of plants of 'Bluebird'.
2. Sterile flowers of plants of the new *Hydrangea* are white to greenish white in color whereas sterile flowers of plants of 'Bluebird' are bluish pink in color.
3. Apices of sterile flowers of plants of the new *Hydrangea* are more acute than and not as rounded as apices of sterile flowers of plants of 'Bluebird'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'HSE1735301' grown in a container.

Figure 2:
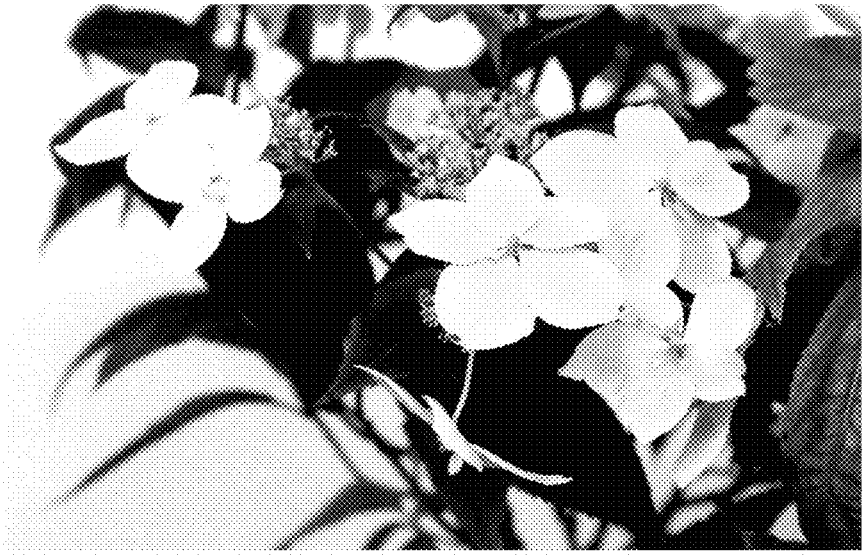

The photograph at the top of the second sheet (FIG. 2) is a close-up view of a typical inflorescence of 'HSE1735301'.

Figure 3:
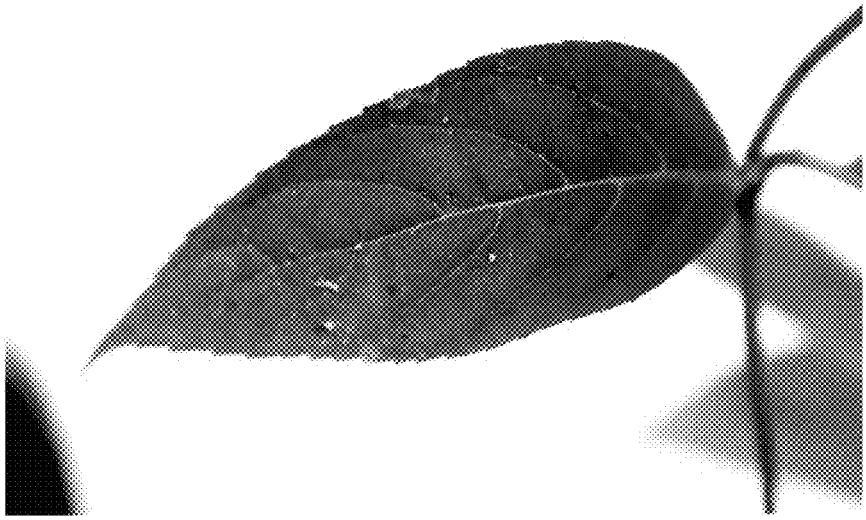

The photograph at the bottom of the second sheet (FIG. 3) is a close-up view of a typical leaf of 'HSE1735301'.

DETAILED BOTANICAL DESCRIPTION

Plants used in the aforementioned photographs and in the following description were grown during the summer in 13-cm containers in an outdoor nursery in Reeuwijk, The Netherlands and under cultural practices typical of commercial *Hydrangea* production. During the production of the plants, day temperatures ranged from 16° C. to 30° C., night temperatures ranged from 8° C. to 18° C. Plants of the new *Hydrangea* were pinched in the early summer. Plants were two years old when the photographs and description were taken. In the following description, color references are made to The Royal Horticultural Society Colour Chart, 2015 Edition, except where general terms of ordinary dictionary significance are used. Mountain *Hydrangea* plants are not typically treated with aluminum sulfate to "blue" the flower color.

Botanical description: *Hydrangea serrata* 'HSE1735301'.

Parentage:

*Female, or seed, patent*.—Proprietary selection of *Hydrangea serrata* identified as code number 12-00-203, not patented.

*Male, or pollen, patent*.—Proprietary selection of *Hydrangea serrata* identified as code number 12-00-205, not patented.

Propagation:

*Type cutting*.—By vegetative terminal cuttings.

*Time to initiate roots, summer*.—About 16 days at temperatures ranging from 20° C. to 30° C.

*Time to produce a rooted young plant, summer*.—About four months at temperatures ranging from 20° C. to 30° C.

*Root description*.—Medium in thickness; fibrous; typically light brown in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Upright to broadly outwardly spreading and mounding plant habit; flattened globular in overall shape; strong and sturdy stems; moderately vigorous growth habit and moderate growth rate; about six months from planting rooted young plants are required to produce small finished plants.

*Plant height*.—About 39.5 cm.

*Plant diameter or area of spread*.—About 53.5 cm.

Lateral branch description:

*Branching habit*.—Freely branching habit with about nine lateral branches developing per plant; pinching is not required, but will enhance lateral branch development.

*Length*.—About 27.9 cm.

*Diameter*.—About 4 mm.

*Internode length*.—About 7 cm.

*Strength*.—Strong, sturdy.

*Aspect*.—Erect to about 65° from vertical.

*Texture*.—Smooth, glabrous; becoming woody with subsequent development.

*Color, developing*.—Close to 143B.

*Color, fully developed*.—Close to 144A and at the internodes, close to 178A; when woody, close to 200C and 200D.

*Lenticels*.—Density: Moderate. Length: About 1.5 mm. Width: About 4 mm. Color: Close to 178A.

Leaf description:

*Arrangement*.—Opposite, simple.

*Length*.—About 13.4 cm.

*Width*.—About 5.1 cm.

*Shape*.—Narrowly elliptic to narrowly oblong.

*Apex*.—Narrowly apiculate.

*Base*.—Short attenuate.

*Margin*.—Serrate.

*Texture, upper surface*.—Slightly rugose, glabrous.

*Texture, lower surface*.—Moderately rugose, glabrous.

*Venation pattern*.—Pinnate.

*Color*.—Developing leaves, upper surface: Close to 138A. Developing leaves, lower surface: Close to a blend of 144A and 146C. Fully developed leaves, upper surface: Close to NN137A to darker than NN137A; towards the margins, tinged with close to 200B; venation, close to 146A. Fully developed leaves, lower surface: Close to 148B; venation, close to 146B.

*Petioles*.—Length: About 1.45 cm. Diameter: About 2.5 mm. Texture and luster, upper and lower surfaces: Smooth, glabrous; slightly glossy. Color, upper surface: Close to 146A to 146B; proximally, tinged with close to 178A. Color, lower surface: Close to 146B; proximally, tinged with close to N199B.

Flower description:

*Flower type and habit*.—Showy rotate sterile and fertile flowers arranged on terminal panicles; panicles flattened lacecap in shape with fertile flowers at the center of the inflorescence surrounded with outer sterile flowers; sterile flowers face upright, outwardly to eventually drooping and fertile flowers face mostly upright.

*Fragrance*.—Moderately fragrant; somewhat moldy.

*Natural flowering season*.—In the garden, plants flower continuously from the early summer to late summer in The Netherlands.

*Flower longevity*.—Good postproduction longevity; sterile flowers maintain good substance for about six weeks on the plant, sterile flowers persistent; fertile flowers last for about five days on the plant, fertile flowers not persistent.

*Quantity of flowers*.—Freely flowering habit; about 7 to 14 sterile flowers and about 150 fertile flowers per panicle.

*Panicle height*.—About 8.3 cm.

*Panicle diameter*.—About 15.7 cm.

*Panicle peduncles*.—Length: About 4 cm. Diameter: About 2 mm. Strength: Strong. Aspect: Primary peduncles, mostly erect; lateral peduncles, about 40° from primary peduncle axis. Texture and luster: Moderately to densely pubescent; matte. Color: Close to 147C.

*Sterile flower buds*.—Length: About 1.2 cm. Diameter: About 9 mm. Shape: Narrowly cup-shaped. Color: Close to N155A.

*Fertile flower buds*.—Length: About 5 mm. Diameter: About 3 mm. Shape: Obovate. Color: Close to 85D and proximally, close to 150D.

*Sterile flower diameter*.—About 5.7 cm.

*Sterile flower depth* (*height*).—About 8 mm.

*Fertile flower diameter*.—About 9 mm.

*Fertile flower depth* (*height*).—About 6 mm.

*Petals, sterile flowers*.—Quantity and arrangement: Four in a single whorl. Length: About 3 mm. Width: About 2 mm. Shape: Ovate; concave. Apex: Acute. Base: Cuneate. Margin: Entire. Texture and luster, upper and lower surfaces: Smooth, glabrous; matte. Color: When opening, upper and lower surfaces: Close to 85D and proximally, tinged with close to 98C. Fully opened, upper and lower surfaces: Close to 85D and proximally, tinged with close to 98C to 98D; color does not change with subsequent development.

*Petals, fertile flowers*.—Quantity and arrangement: Five in a single whorl. Length: About 3 mm. Width: About 2 mm. Shape: Ovate, concave. Apex: Acute. Base: Cuneate. Margin: Entire. Texture and luster, upper and lower surfaces: Smooth, glabrous; matte. Color: When opening, upper surface: Close to 85D and proximally, tinged with close to 98C. When opening, lower surface: Close to 85D and proximally, slightly tinged with close to 98D. Fully opened, upper and lower surfaces: Close to 85D and proximally, slightly tinged with close to 98D; color does not change with subsequent development.

*Sepals, sterile flowers*.—Quantity and arrangement: Typically four, or occasionally five, arranged in a single whorl. Length: About 3 cm. Width: About 2.3 cm. Shape: Broadly elliptic to close to rhomboidal; flat. Apex: Short apiculate to abruptly acute. Base: Cuneate. Margin: Crenate; slightly undulate. Texture and luster, upper and lower surfaces: Smooth, glabrous; matte. Color: When opening, upper and lower surfaces: Close to NN155A. Fully opened, upper surface: Close to 157C and towards the margins, close to NN155C; with subsequent development, color becoming closer to 145B. Fully opened, lower surface: Close to 157B and towards the margins, close to NN155B; with subsequent development, color becoming closer to 145B.

*Sepals, fertile flowers*.—Quantity and arrangement: Five in a single whorl. Length: About 1 mm. Width: About 1 mm. Shape: Deltoid. Apex: Broadly acute. Base: Broadly cuneate. Margin: Entire. Texture and luster, upper and lower surfaces: Smooth, glabrous; matte. Color: When opening and fully opened, upper surface: Close to 150D slightly tinged with close to N170D; color does not change with subsequent development. When opening and fully opened, lower surface: Close to 150D slightly tinged with close to N170D; color does not change with subsequent development.

*Pedicels, sterile flowers*.—Length: About 2.7 cm. Diameter: About 1 mm. Strength: Moderately strong. Aspect: About 25° from main peduncle axis. Texture and luster: Densely pubescent; matte. Color: Close to 146D.

*Pedicels, fertile flowers*.—Length: About 2 mm. Diameter: About 1 mm. Strength: Moderately strong. Aspect: About 20° from vertical. Texture and luster: Smooth, glabrous; matte. Color: Close to 85D tinged with close to 150D.

*Reproductive organs, sterile flowers*.—Stamens: Quantity per flower: About ten. Filament length: About 2 mm. Filament color: Close to N88B. Anther shape: Broadly double oblong. Anther length: About 0.75 mm. Anther color: Close to 94C to 94D. Pollen amount: Sparse. Pollen color: Close to NN155B. Pistils: Pistil quantity per flower: Three, or occasionally, two. Pistil length: About 1 mm. Stigma shape: Club-shaped. Stigma color: Close to 192A. Style length: About 0.5 mm. Style color: Close to 92C. Ovary color: Close to 92A.

*Reproductive organs, fertile flowers*.—Stamens: Quantity per flower: Ten. Filament length: About 2 mm. Filament color: Close to NN155D. Anther shape: Broadly double oblong. Anther length: About 0.8 mm. Anther color: Close to 102D to lighter than 102D. Pollen amount: Sparse. Pollen color: Close to NN155B. Pistils: Pistil quantity per flower: Three, or occasionally, four. Pistil length: About 1 mm. Stigma shape: Club-shaped. Stigma color: Close to 92A. Style length: About 0.5 mm. Style color: Close to 92C. Ovary color: Close to 150D.

*Seeds*.—To date, seed development has not been observed on plants of the new *Hydrangea*.

Pathogen & pest resistance: Plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HSE1735301' as illustrated and described.

* * * * *